(12) United States Patent
Kurabayashi et al.

(10) Patent No.: US 7,105,355 B2
(45) Date of Patent: Sep. 12, 2006

(54) FLOW CYTOMETERS AND DETECTION SYSTEM OF LESSER SIZE

(75) Inventors: Katsuo Kurabayashi, Ann Arbor, MI (US); Shuichi Takayama, Ann Arbor, MI (US); Steven J. Skerlos, Ann Arbor, MI (US); Dongeun Huh, Stanford, CA (US); James B. Grotberg, Ann Arbor, MI (US); Yi-Chung Tung, Ann Arbor, MI (US)

(73) Assignee: The Regents of the University of Michigan, Ann Arbor, MI (US)

( * ) Notice: Subject to any disclaimer, the term of this patent is extended or adjusted under 35 U.S.C. 154(b) by 420 days.

(21) Appl. No.: 10/198,378

(22) Filed: Jul. 18, 2002

(65) Prior Publication Data

US 2003/0054558 A1    Mar. 20, 2003

Related U.S. Application Data (60) Provisional application No. 60/306,382, filed on Jul. 18, 2001.

(51) Int. Cl.
*G01N 21/03* (2006.01)
*G01N 21/63* (2006.01)

(52) U.S. Cl. .................. 436/165; 436/63; 436/164; 436/180; 422/73; 422/82.05; 422/82.09; 422/82.11

(58) Field of Classification Search .............. 436/63, 436/164, 165, 172, 180, 181; 422/73, 81, 422/82.05, 82.08, 82.09, 82.11, 83
See application file for complete search history.

(56) References Cited

U.S. PATENT DOCUMENTS

| | | | |
|---|---|---|---|
| 4,140,902 A | 2/1979 | Young | |
| 4,906,095 A | 3/1990 | Johnston | |
| 4,983,038 A * | 1/1991 | Ohki et al. | 356/246 |
| 5,122,284 A * | 6/1992 | Braynin et al. | 210/782 |
| 5,144,224 A | 9/1992 | Larsen | |
| 5,257,633 A * | 11/1993 | Vogler et al. | 600/576 |
| 5,270,548 A | 12/1993 | Steinkamp | |
| 5,315,122 A | 5/1994 | Pinsky et al. | |
| 5,317,162 A | 5/1994 | Pinsky et al. | |
| 5,404,749 A | 4/1995 | Spangler | |
| 5,488,864 A | 2/1996 | Stephan | |
| 5,504,337 A | 4/1996 | Lakowicz et al. | |
| 5,674,698 A | 10/1997 | Zarling et al. | |
| 5,698,397 A | 12/1997 | Zarling et al. | |
| 5,736,410 A | 4/1998 | Zarling et al. | |
| 5,891,656 A | 4/1999 | Zarling et al. | |
| 6,097,485 A * | 8/2000 | Lievan | 356/338 |
| 6,159,686 A | 12/2000 | Kardos et al. | |

(Continued)

FOREIGN PATENT DOCUMENTS

EP    0286088    10/1988

(Continued)

OTHER PUBLICATIONS

J. Crossland-Taylor, NATURE, 171, 37-38 (1953).

(Continued)

*Primary Examiner*—Maureen M. Wallenhorst
(74) *Attorney, Agent, or Firm*—Brooks Kushman P.C.

(57) ABSTRACT

Gas focusing flow cytometers are fabricatable employing simple and inexpensive manufacturing techniques. When such cytometers or conventional cytometers are combined with fiber optical light paths and laser diode and semiconductor photodetectors, light weight and handheld, optionally disposable devices which maintain high performance are possible.

2 Claims, 7 Drawing Sheets

U.S. PATENT DOCUMENTS

| | | |
|---|---|---|
| 6,309,886 B1 | 10/2001 | Ambrose et al. |
| 6,312,914 B1 | 11/2001 | Kardos et al. |
| 6,337,213 B1 | 1/2002 | Simon et al. |
| 6,382,228 B1 | 5/2002 | Cabuz et al. |
| 6,399,397 B1 | 6/2002 | Zarling et al. |
| 6,597,438 B1 | 7/2003 | Cabuz et al. |
| 6,787,104 B1 | 9/2004 | Mariella, Jr. |
| 2003/0175687 A1 | 9/2003 | Tippet |

FOREIGN PATENT DOCUMENTS

| | | |
|---|---|---|
| EP | 0 463 562 A1 | 1/1992 |
| WO | WO 85/05680 | 12/1985 |

OTHER PUBLICATIONS

D.S. Stein et al., J. Infect. Dis., 165 (2), 352-63 (1992).

D. Fenili et al., Clin. Chem. Lab. Med., 36 (12), 909-17 (1998).

C.L. Harding et al., "Cell Biology," Biotechnol. Prog., 16 (5), 800-02 (2000).

K.A. Criswell et al., "Toxicology," CYTOMETRY, 32 (1), 18-27 (1998).

G.B.J. Dubelaar, Scientia Marina, 64 (2), 255-65 (2000).

Y.N. Xie et al., SCIENCE, V. 273 p. 347 ff (1996).

Y.N. Xia et al., "Soft Lithography," Annu. Rev. Matter Sci V. 28, pp. 153-184 (1998).

B. Zhao, "Surface Directed Liquid Flow Inside Microchannels," SCIENCE, 291, pp. 1023-1026, 2001.

Huh et al., "Use of Air-Liquid Two-Phase Flow in Hydrophobic Microfluidic Channels for Disposable Flow Cytometers," Biomedical Microdevices, 4 (2), 141-49 (2002).

S. Takayama, "Chemoenzymatic Preparation of Novel Cyclic Imine Sugars and Rapid biological Activity Evaluation Using Electrospray Mass Spectometry and Kinetic Analysis," J. Am. Chem. Soc., 119, pp. 8146-8151 (1997).

Abstract corresponding to EP 0 463 562 A1.

Citation from Biological Abstracts: B01 Using The Microcyte Flow Cytometer to Monitor Cell Number, Viability, and Apoptosis In Mammalian Cell Culture. BIO 03-49 03-504285 NDN-199-0079-4023-2.

Citation from European Fulltext Applications: EFA Portable Flow Cytometer: EPA Mar. 3, 2004 01393143/EP-A2 NDN-113-0208-6477-4.

Citation from INSPEC;INS "Towards Portable Flow Cytometery: Study On the Use of Air-Sheath-Based Volume-Efficient Two-Phase Microfluidic Systems" INS 03-16, 7597413 A2003-11-8780-035 (PHA) NDN-259-0759-7412-3.

Citation from INSPEC:INS Development Of A Microdluidic Device For Fluorescence Activated Cell Sorting: INS 02-38 7393055 A2002-21-8780B-009 (PHA); B2002-11-7230J-007 (EEA) NDN-259-0739-3054-9.

Citation from Life Sciences Collection (LSC); LSC "A Low-Cost, Portable Flow Cytometer Specifically Designed For Phytoplankton Analysis". LSC 90-10 2309470 NDN-122-008-3830-2.

Citations from NASA STAR: NAS "Evaluation of Optoflow Microcyte (registered) Flow Cytometer" NAS 02-07 22020053657 NDN-117-0318-3665-5.

Citation from World Patent Full Text: PCN "Optical Detection System For Flow Cytometry" PCN Feb. 7, 2002 2002010874/WO-A3 NDN-263-0333-1292-1.

Citation from World Patent Full Text: PCN "Portable Flow Cytometer" PCN Feb. 7, 2002 2002010713/WO-A2 NDN-263-0333-0667-5.

Citation from US Patent Fulltext:: USF "Portable Flow Cytometry" PAT Jul. 22, 2003 06597438 NDN-269-3074-3704-7.

Citation from US Patent Fulltext: USF "Fluid Driving System For Flow Cytometry" PAT May 7, 2002 06382228 NDN-269-2981-0865-6.

Citation from US Patent Fulltext: USF "Apparatus and Method For Collection and Concentration of Respirable Particles Into a Small Fluid Volume" PAT Jan. 8, 2002 06337213 NDN-269-2961-7078-1.

Citation from US Patent Fulltext: USP "Microchip Optical Transport Technology For Use In A Personal Flow Cytometer" PAT Aug. 1, 2000 06097485 NDN-269-2857-7498-1.

Abstract "Optical Characterization In Flow Cytometry: Optimization and Miniaturization" DIS 96-02 AAIC447619 NDN-135-0219-5322-3.

Abstract "A Semiconductor Microlaser For Intracavity Flow Cytometry" EDB 99-18 99:080743 00000003291 NDN-108-0672-7817-7.

Abstract "Closed Sample Cell For Use In Flow Cytometry" EPA Jan. 2, 1992 0463562/EP-A1 NDN-113-0032-0370-1.

Patent Abstracts of Japan, vol. 13, No. 375 (P-921), Aug. 21, 1989 & JP 129161 A (Hitachi Ltd.), May 22, 1989 Abstract.

Patent Abstracts of Japan, vol. 14, No. 325 (P-1075), Jul. 12, 1990 & JP 02 107945 A (Fuji Electric Co. Ltd), Apr. 19, 1990 Abstract.

* cited by examiner

FLOW CYTOMETERS AND DETECTION SYSTEM OF LESSER SIZE

CROSS-REFERENCE TO RELATED APPLICATION

This application claims the benefit of U.S. provisional application Ser. No. 60/306,382, filed Jul. 18, 2001.

BACKGROUND OF THE INVENTION

1. Field of the Invention

The present invention is directed to flow cytometers.

2. Description of the Related Art

Flow cytometers are useful in the detection of particulates in liquid systems, in particular for the detection and/or identification of microbes, including pathogens. Flow cytometry per se is a mature technology. Flow cytometers concentrate a particulate-containing inlet stream to a relatively small diameter "observation" stream in which the particles pass "single file" past a detector located in an observation channel. Focusing of the liquid sample is achieved by injecting a liquid as a sheath surrounding the stream of sample. The necessity for a rather large volume of liquid relative to the volume of sample contributes to the overall size of the device, and with biological samples suspected of containing pathogens, contributes to waste disposal problems. Reducing complexity by eliminating liquid focusing has been attempted, J. Crosland-Taylor, NATURE 171, 37–38 (1953), but has not been regarded as successful, due to deficiencies such as channel clogging and slow velocity of sample flow which reduces the optical detection rate. Thus, current flow cytometers employ liquid focusing.

Typical flow cytometers are bench scale devices comprising a flow cytometer cell, a laser light source, and a photomultiplier detector. In order to produce an acceptable signal to noise ratio, the detection system also includes a dichroic beam splitter, focusing optics, and a combination of photodiode and photomultiplier. A typical flow cytometer is represented schematically in FIG. 1. The most compact commercial instruments occupy more than 2 ft$^3$ (ca. 0.07 m$^3$) of space, and are quite expensive. Typical flow cells are constructed of quartz, and alone cost ca. U.S. $3500 (2002) and thus are clearly not disposable. The optical components of the detection system are major contributors to the overall cost, as are the laser and photomultiplier.

Flow cytometers have gained widespread use in a variety of medical, scientific, and engineering fields such as disease diagnosis and monitoring, D. S. Stein et al., J. INFECT. DIS. 165 (2), 352–63 (1992); D. Fenili et al. CLIN. CHEM. LAB. MED., 36 (12), 909–17 (1998), cell biology C. L. Harding, et al., BIOTECHNOL. PROG. 16 (5), 800–02 (2000), toxicology, K. A. Criswell, et al., CYTOMETRY 32 (1), 18–27 (1998), and environmental monitoring, G. B. J. Dubelaar, SCIENTIA MARINA 64 (2), 255–65 (2000). Flow cytometers have been used in monitoring of white blood cells for HIV infection, and for monitoring of dialysis fluids and the like. Use of flow cytometers is also being increasingly investigated in view of threats of biological contamination, not only due to terrorist activities, but also due to increased contamination of water supplies caused by steadily increasing population density.

It would be desirable to provide flow cytometers which occupy less physical space, to the extent, for example, of providing hand held devices. It would further be desirable to provide flow cytometers which do not rely on liquids as the focusing fluid, and which utilize less expensive, and less bulky detection devices. It would be desirable to provide flow cytometer cells which are disposable as a practical matter.

SUMMARY OF THE INVENTION

It has now been surprisingly discovered that the focusing fluid of conventional flow cytometers can be replaced by a gas stream while maintaining substantially non-turbulent flow through an observation zone. It has been further surprisingly discovered that the complex, expensive, and bulky laser/photomultiplier detection system can be eliminated by relying on laser diodes in conjunction with PIN photodiodes for detection, preferably in conjunction with fiber optic light impingement and collection pathways. The latter system is capable of use with either gas-focusing or conventional liquid-focusing flow cytometers. Preferred flow cytometer cells are disposable, and can be configured for either gas or liquid focusing. Multi-directional light source and/or detection can be used to maximize signal to noise ratios and to increase the number of particle parameters which can be measured. Devices with geometries similar to gas-focusing flow cytometer cells but with hydrophilic surfaces may be used in applications where atomization of a fluid stream is desired.

DETAILED DESCRIPTION OF THE PREFERRED EMBODIMENT(S)

The flow cytometers of the present invention are best described in terms of conceptual components: a flow cell, a light source, a light impingement system, a light collection system, and a detector system. These components will be described separately, and may be configured in numerous permutations, as will be evident hereafter.

The flow cells and detection systems associated therewith may take the form of numerous embodiments. Thus, in one broad aspect, the subject invention pertains to flow cells which may be used to focus a liquid stream with the aid of at least one gas focusing stream. Such flow cells have numerous uses, of which flow cytometry is one example. The subject invention further pertains to novel detection systems usable with these and other flow cytometers, including liquid focusing flow cytometers.

In a further aspect of the invention, a detection system is provided which contains a light source comprising a plurality of laser diodes and/or LEDs which generate at least two different "monochromatic" wavelengths, i.e. a single wavelength or a relatively narrow band of wavelengths, these two different monochromatic wavelengths in communication with a single fiber optic light impingement path, and a detector system which may be a single photodetector sensitive to all monochromatic wavelengths without being able to discriminate between wavelengths; a single photodetector-sensitive to all monochromatic wavelengths and capable of distinguishing between at least two of the monochromatic wavelengths; a plurality of semiconductor detectors sensitive to at least one but not all of the monochromatic wavelengths, each of these detectors in communication with a separate light collection path; or a combination thereof.

In a yet further aspect of the invention, disclosed is a detector system suitable for use with a fiber optic impingement and/or collection path flow cytometer cell wherein at least one wavelength is supplied to an interrogation zone in a definable repetitive manner, the detector system comprising at least one semiconductor detector, and an amplification system for amplifying a signal from the detector. An output of the amplifier is selected synchronously with the repetitively generated light. The light source comprises a laser diode or a preferably filtered LED device, the light conveyed by means of a fiber optic light impingement path of the flow cell.

In still another embodiment of the invention, disclosed is a method for maximizing the signal to noise ratio of a flow cell apparatus having a flow cell containing an interrogation zone and associated with at least one light source and at least one light detector, this method comprising providing a fiber optic light impingement path which terminates at or proximate to the interrogation zone, and a plurality of fiber optic collection paths terminating internally at or proximate to the interrogation zone which selectively communicate with a photodetector; monitoring the photodetector output of each of a plurality of combinations of impingement/collection paths; and selecting a specific combination of impingement/collection paths which provides a high signal to noise ratio over time with respect to at least one other combination of infringement/collection paths, or recording outputs of a plurality of impingement/collection paths and selecting, for any point in time, the specific impingement/collection path with the highest signal to noise ratio at that point in time.

The flow cell may be disposable or non-disposable. Disposable flow cells which can be used but once or for a limited number of analyses are preferred.

Figure 1:
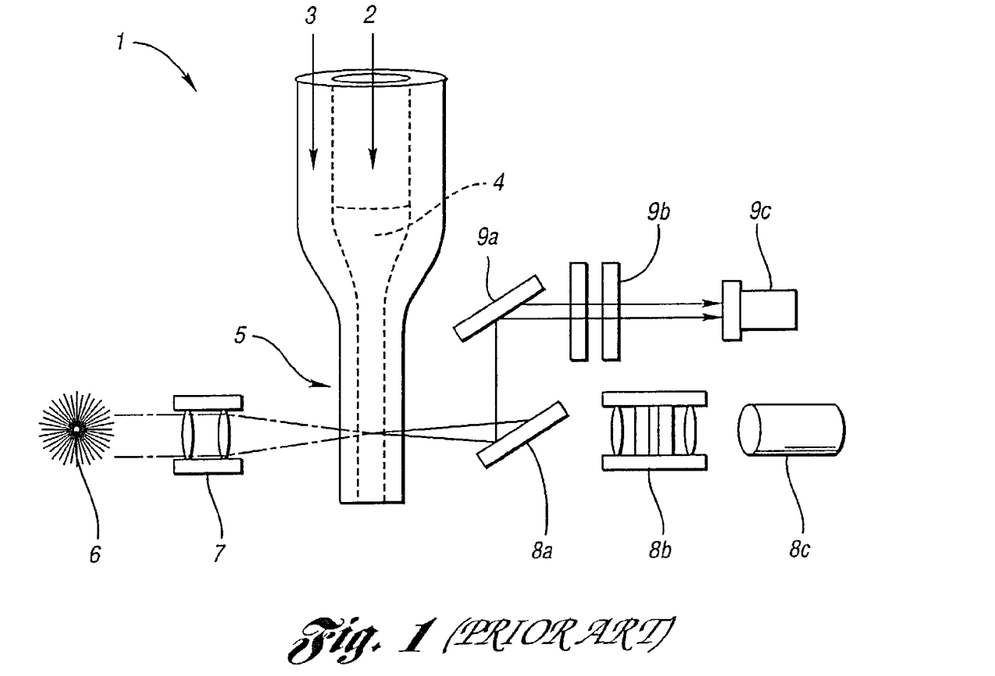
FIG. 1 illustrates a typical, liquid focusing flow cytometer and photomultiplier tube detection system.

One important embodiment of the present invention is a flow cell which employs gas rather than liquid as the focusing medium. As shown in FIG. 1, in conventional liquid flow cytometers 1, the liquid stream 2 to be analyzed is fed to the device centrally, surrounded by a large flow of focusing liquid as a "sheath" 3. The passageway which the sample stream and focusing stream enters is substantially conical, and the streams narrow as they traverse this conical transition 4 into the observation chamber, or "interrogation zone" 5. Due to substantially laminar flow, the sample stream narrows to the point where particulates tend to pass "single file" through the zone, surrounded by the focusing fluid sheath. The focusing fluid supply is many times the volume of sample fluid, typically from 250 mL to 1 L per mL of sample fluid, which contributes to the size of conventional flow cytometers as well as generating disposal problems. Recycling of focusing liquid has been proposed, but requires additional complexity and microfiltration. Furthermore, recycling is impractical when the sample liquid contains substances soluble in the focusing liquid. The absorbency of the sheath fluid also may decrease sensitivity unless it is optically transparent at the wavelengths of interest. Passage of particles, detected by light blocking, scattering, or fluorescence of tagged particles, is achieved by focusing light from laser 6 through focusing optics 7 through the interrogation zone 5. Light from the interrogation zone is split by dichroic beam splitter 8a and directed by suitable optics and filters 8b to photomultiplier tube 8c. A split path is directed by mirror 9 through suitable filters 9b to photodiode 9c.

Gas cannot be employed as a focusing fluid in conventional flow cytometer cells because the impingement of gas with the liquid sample stream causes the latter to break up, thus preventing establishment of a defined flow stream. For example, if one were to attempt to use gas as a "sheath" or "focusing" fluid in a conventional flow cytometer rapid breakup of the liquid sample stream and flow of the liquid sample along the walls of the interrogation zone rather than being concentrated as a single, centrally located stream within this zone with results. It has now been discovered that a gas stream may be used as a focusing fluid if the passageways of the flow cell are rendered hydrophobic, at least over the portions of the flow cell where gas and liquid streams will be present. It has also been discovered that flow cells may be inexpensively produced from thermosettable polymers or of thermoplastics rather than relatively expensive materials such as quartz or fused silica, although the latter as well as other substrates may also be used, so long as a hydrophobic surface is provided.

Figure 2:
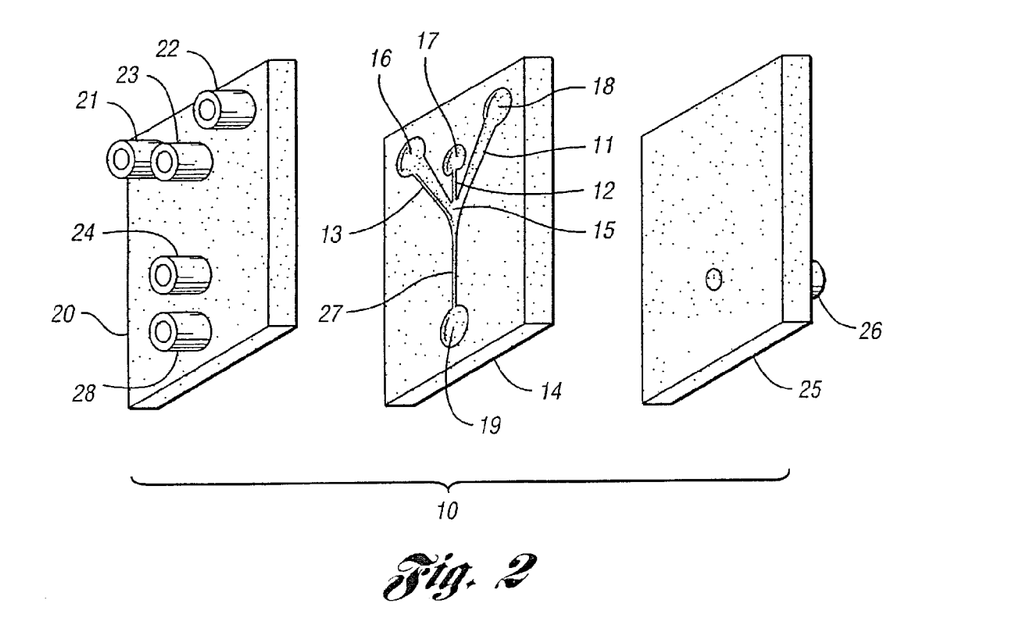
FIG. 2 illustrates one embodiment of a gas-focusing flow cytometer cell of the present invention.
Figure 3:
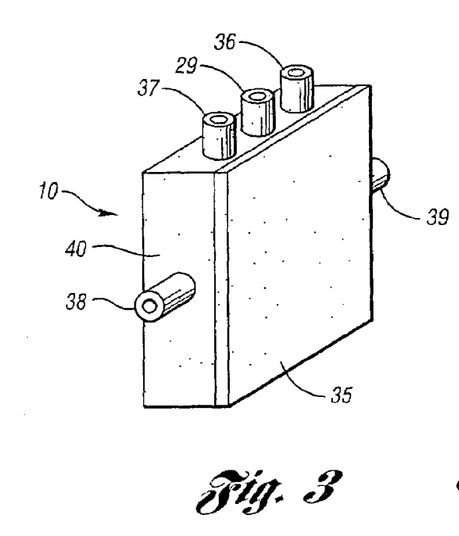
FIG. 3 illustrates a hand holdable flow cytometer.

A typical two dimensional focusing flow cell is illustrated in FIGS. 2 and 3. In FIG. 2, a three piece embodiment of a flow cell 10 is depicted. The flow channels 11, 12, and 13 are contained in the middle layer 14, and supply focusing gas through channels 11 and 13, and sample liquid through channel 12, to the focusing zone 15. At the top of each channel is located an optional supply reservoir (16, 17, 18), generally of larger size to simplify connective pathways for supply of the various fluids and to stabilize fluid dynamic behavior at the channel inlets. Following the focusing zone 15 is an outlet reservoir 19.

Leftmost layer 20 contains gas inlets 21 and 22 which are in communication, following assembly of the flow cell, with gas supply reservoirs 16 and 18, respectively. It is also possible, and preferred, to use but one gas inlet which communicates with all gas supply reservoirs, or directly with the gas channels should reservoirs or equivalent structure be absent. Leftmost layer 20 also contains a sample inlet 23 in fluid communication with sample reservoir 17 and/or channel 12, and an outlet 28 in fluid communication with outlet reservoir 19. Also included is light source connector or supply 24, as more fully described hereafter. Rightmost layer 25 contains light detector connector or passageway 26, as more fully described hereafter. The focusing zone 15 transitions to interrogation zone 27, located between connector or light source 24 and detector or passageway 26.

The entire device may be constructed of a hydrophobic polymer such as polydimethylsiloxane (PDMS), or may be constructed of alternative materials, including conventional thermosetting polymers, thermoplastics, glass, ceramic, metal, and the like, provided that the portions of the internal passageways of the device preceding and including the interrogation zone where both liquid and gas are simultaneously present have hydrophobic surfaces, and that the device is transparent to the wavelengths of interest in an area between the light source and the detector within the interrogation zone, so that light scattered by particles passing through the interrogation zone can be analyzed appropriately as in conventional flow cytometers.

A convenient method of constructing the focusing chamber, interrogation zone, and further channels and reservoirs is the use of soft lithography as disclosed by Y. N. Xia et al., SCIENCE, V. 273 p.347 ff (1996). The use of this technique also allows a simple lens or even a grating to be fabricated in the device. Y. N. Xia et al., "SOFT LITHOGRAPHY" Annu. Rev. Matter SC1 V. 28, pp 153–184, (1998). The lens and grating may form part of the wall of the interrogation zone, for example, for light focusing and/or collimation or spectral dispersion.

For example, the central layer 14 and outer layers 20 and 25 may all be cast or injection molded of PDMS. Alternatively, the central layer 14 may be constructed of PDMS and the outer layers 20, 25 made of injection molded polymer such as an acrylate polymer, or of metal, glass, etc. Prior to assembly, the portions of the outer layers 20, 25 which will form a portion of the walls of the various flow channels and interrogation zone are preferably hydrophobicized if not constructed of hydrophobic polymer. For example, a hydrophobic layer of polytetrafluoroethylene may be applied, or treatment with a hydrophobicizing agent such as a reactive fluorochemical, or a reactive hydrophobic silane such as octyldimethylmethoxysilane, trimethylmethoxysilane, tris (perfluoropropyl)methoxysilane, or the like may be applied. Hydrophobicizing reagents and processes for their application are well known. Further methods of hydrophobicizing are disclosed in B. Zhao, "Surface Directed Liquid Flow Inside Microchannels," SCIENCE, 291, pp.1023–26, 2001.

If outer layers 20, 25 are of non-transparent material, i.e. metal, a transparent observation port, passage, or optical waveguide must be provided in these layers to allow detection. For example, a passage may be cast or machined in the respective layers, this passage being terminated by a transparent window or lens system, as disclosed in FIGS. 4 and 5, a side view through one of the outermost layers through an area containing the "observation port"

Figures 4, 5:
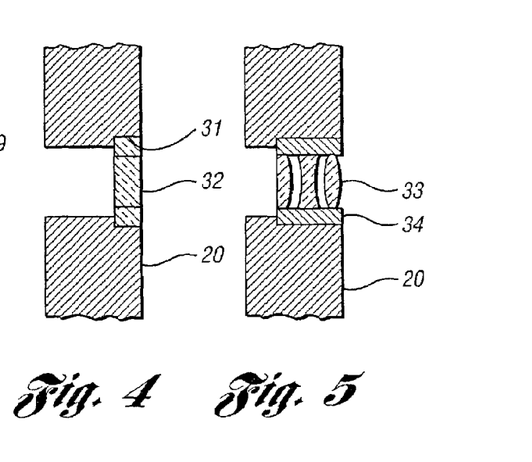
FIG. 4 illustrates one embodiment of a light impingement and/or collection pathway of a flow cytometer cell device of the present invention.
FIG. 5 illustrates a further embodiment of a light impingement and/or collection pathway of a flow cytometer cell device of the present invention.

In FIG. 4, the layer 20 contains a recess 31 into which window 32 is set, for example by interference fit, by adhesively securing, etc., here shown abutting a step in the recess. In FIG. 5, a prefabricated lens assembly is shown, consisting of a triplet lens system 33 assembled within a sleeve 34. The window may also advantageously be of plastic, fluorite, quartz, sapphire, or other material transparent to the wavelengths of interest.

In FIG. 3, a completely assembled, layered device is shown, this device consisting of but two layers. In this device, outermost layer 35 of device 10 serves only as a cover for the various internal channels, while the gas inlets 36, 37, sample inlet 29, light source/connector 38, and light detector/connector 39 are all molded into the "body" 40 of the device.

Figure 6A:
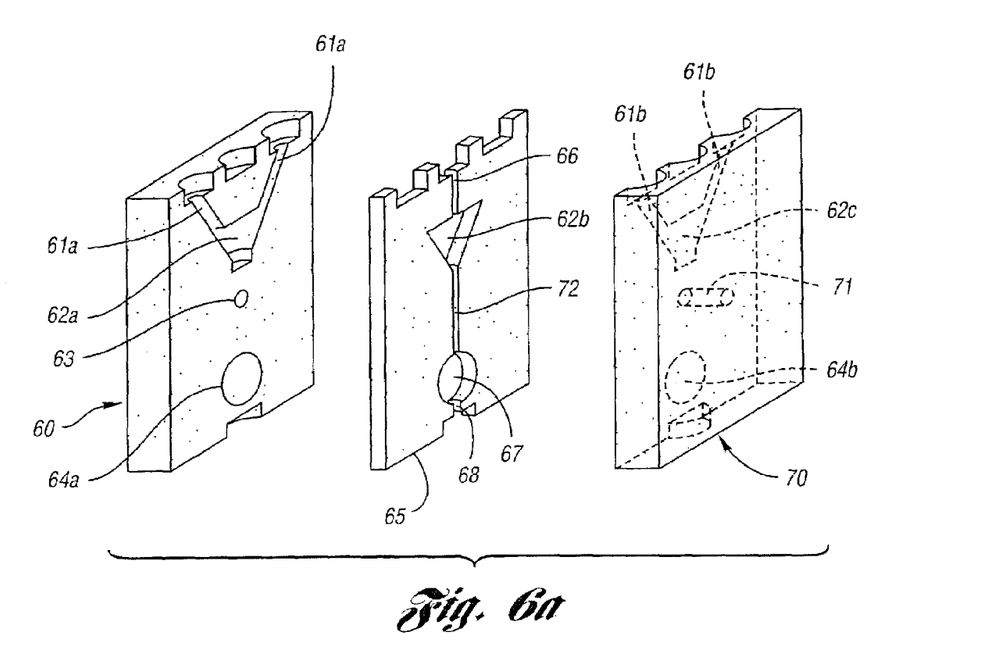
FIGS. 6a and 6b illustrate embodiments of a molded, three dimensional gas focusing flow cytometer cell of the present invention.
Figure 6B:
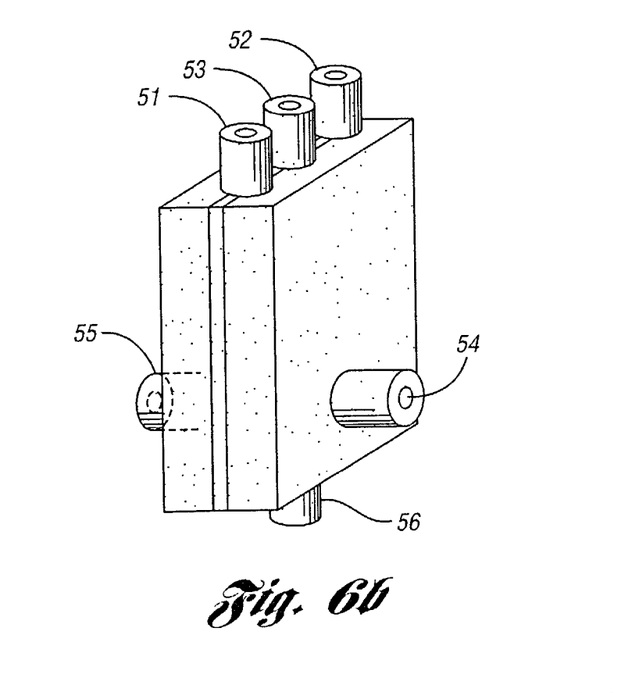

A device may also be constructed of micromachinable substances such as silicon or silica by conventional semiconductor processing techniques. For example, a glass or silicon substrate may be chemically etched or etched by plasma techniques, etc., to contain the necessary channels, interrogation zone, etc., on its surface. "Three dimensional" micromachined devices may be created by combinations of etching, material deposition, further deposition, etc. These steps are well known to those skilled in the art of micromachining. Reference may be had to U.S. Pat. Nos. 5,404,749 and 5,488,864, for example, wherein torsion beam accelerometers are fabricated on a silicon substrate. Internal passages can be hydrophobicized following completion of the device by exposure to hydrophobicizing reagents. For mass production of numerous devices at economical production cost, injection molding processes may be used to provide one or more components of the flow cells. In FIGS. 6a and 6b, an injection molded, three dimensional-focusing device is illustrated.

In FIG. 6a, a three part construction is shown. In leftmost layer 60, the inner face contains gas channels 61a which communicate with leftmost portion of focusing zone 62a. A passage 63 allows for entry of detecting light, and near the bottom is leftmost portion of outlet reservoir 64a. A middle layer 65 contains the bulk of the focusing zone 62b and a sample fluid passage 66 in communication therewith. The focusing zone communicates with the interrogation zone 72 which communicates with the bulk of the outlet reservoir 67 and outlet passage 68. The rightmost layer 70 is, in this case, a mirror image of leftmost layer 60, and contains gas passages 61b, rightmost focusing zone portion 62c, light detection passage 71, and leftmost outlet reservoir portion 64b.

The terminations of the various channels external to the device are advantageously adapted to be single plug-in connectors as are common for supply of fluids, or in the case of the connectors for the light supply and detector passageways, simple snap fittings which allow suitable coupling to external light emitters (lasers, laser diodes, etc.) and detectors (photomultiplier tubes, PIN diodes, etc). In preferred devices, these latter companies may be incorporated into the body of the cell, such that only electrical connections (electrical contacts, jacks, coaxial cable), etc., may be required.

An assembled device of FIG. 6a is depicted in FIG. 6b, where gas focusing supply connectors 51, 52 communicate with the focusing gas passages formed by the combination of passages 61a, 61b, and are connectable by standard (or non-standard) fittings to a supply of gas, and sample fluid connector 53 communicates with fluid passage 66 and is similarly connectable to a sample fluid supply. Connectors 54 and 55 allow light to enter and leave the device, and may be standard fiber optic coupling devices when fiber optic waveguides are employed, or may be threaded or snap in connectors when a light path is provided internally. Connector 56 communicates with outlet passage 68 and is connectable to outlet tubing or other devices which enable disposal of fluid.

Figure 7:
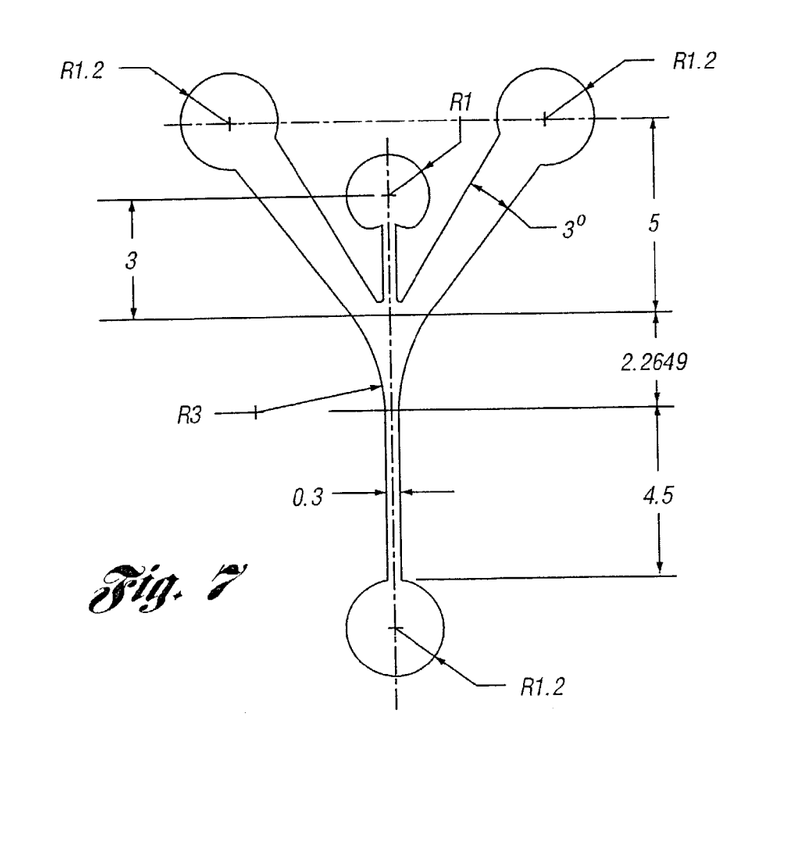
FIG. 7 illustrates dimensions for one embodiment of a gas focusing flow cytometer.
Figure 8:
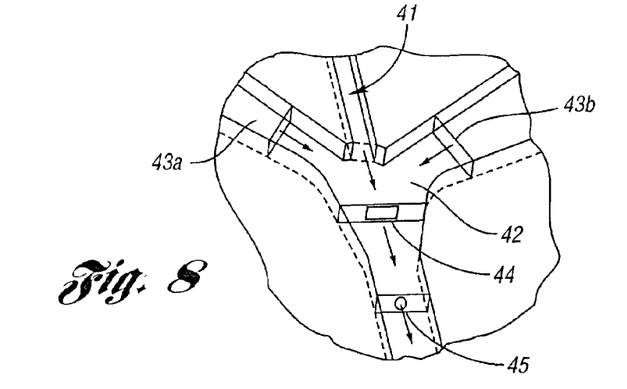
FIG. 8 illustrates the focusing achieved in a two dimensional gas focusing flow cytometer of the present invention.

The geometry of the focusing chamber, interrogation zone, etc., is such that the sample stream is focused, either two dimensionally or multiply dimensionally, without substantial breakup of the sample stream when used as a flow cytometer. Numerous geometries are possible, and the various channel chambers and zones may take numerous cross-sections. A suitable geometry is provided in FIG. 7, which should not be construed as limiting. Dimensions are in mm. Focusing of the sample fluid is illustrated in FIG. 8, wherein sample fluid stream 41 enters focusing chamber 42 together with air sheaths or "focusing streams" 43a and 43b. As the focusing chamber narrows, the sample stream is altered in shape and constricted 44 to a narrow and coherent stream 45 within the interrogation zone.

In a typical device, the diameter of the liquid sample channel may be from 1–1000 μm, preferably 10–300 μm, and most preferably about 20 μm at the downstream end where it communicates with the focusing chamber. The gas channels at this point are preferably somewhat larger in dimension, for example 200–600 μm, preferably 250–500 μm, and more preferably 300–400 μm, and converge with the fluid sample channel at an acute included angle, preferably from 15–45°, more preferably 20–40°, and most preferably ca. 30°. The walls of the focusing chamber are defined by the outer walls of the gas inlet channels at its "upper" end, for example 1000 μm to 2000 μm, preferably about 1500 μm, and at the "lower" end, by the diameter of the interrogation zone into which the focusing chamber transitions, i.e. from 100 μm to 500 μm, preferably 200 μm to 400 μm, and most preferably about 300 μm. The transition of the upper end of the focusing chamber to the lower end, the beginning of the interrogation zone, is roughly V-shaped in plan, and the side walls may be slightly concave, as described in the figures, the actual geometry being straight, circular, elliptical, hyperbolic, parabolic, or other shape which suitably minimizes breakup of the sample stream.

The liquid sample and focusing gas flow rates are selected so as to form a focused but coherent liquid sample stream within the interrogation zone of the desired diameter. It should be noted that the fluid sample is not necessarily completely enveloped by gas, although complete envelopment is preferred. The diameter of the sample stream in the interrogation zone will be a function of the gas flow rate, the liquid sample flow rate, and the vacuum (if any) applied at the outlet. The lower end of the interrogation zone, for example the outlet reservoir, is preferably maintained at less than atmospheric pressure, for example from 10 mm Hg to 700 mm Hg. A pressure of 45 mm Hg has been found quite suitable. Alternatively, the inlet reservoirs could be maintained at positive pressure without requiring application of vacuum at the outlet. The physical geometry of the device may also affect sample stream diameter.

For example, the gas flow rate may range from 40 mL/hr to 15,000 mL/hr, preferably ca. 800 mL/hr. At these gas flow rates, with a 45 mm Hg vacuum, and in a channel with a 100 μm height, the diameter of the focused liquid sample stream in the interrogation zone may be varied from as little as 15 μm at a liquid sample flow rate of 6 mL/hr to about 100 μm at a flow rate of 20 mL/hr. Calculations based on fluid dynamics indicate that in a device with a 300 μm wide interrogation zone, a gas flow rate of about 700–900 mL, and a vacuum at the outlet of 45 mm Hg, the maximum focused liquid stream flow rate is approximately 50 mL/hr, at which point the liquid will contact the walls of the interrogation chamber. These same calculations indicate a minimum sample flow rate of 6.6 mL/hr without losing stream coherency. A stable 6 mL/hr stream has been observed. However, lowering the flow rate to 5 mL/hr caused the stream to be discontinuous. The geometry and dimensions of the channel can be tailored to achieve stability at different flow rates. For further discussion of the necessary calculations, reference may be made to Huh, et al., "Use of Air-Liquid Two-Phase Flow in Hydrophobic Microfluidic Channels for Disposable Flow Cytometers," BIOMEDICAL MICRODEVICES, 4 (2), 141–49 (2002), based on the work of the present inventors.

In various microfluidics applications, it may be desirable to atomize a fluid inlet stream rather than to focus the stream as is necessary for flow cytometry. Examples include applications such as microcarburation, heterophase oxidations, reductions, and hydrogenations, and gas exchange systems where exchange of gas to or from a liquid is desired. Hydrogenation employing platinum catalysts in an aqueous system is disclosed by S. Takayama, "Chemoenzymatic Preparation of Novel Cyclic Imine Sugars and Rapid Biological Activity Evaluation Using Electrospray Mass Spectometry and Kinetic Analysis," J. AM. CHEM. SOC., 119, pp. 8146–51 (1997). The high surface area generated by atomization can facilitate hydrogen transfer in such systems. With blood as a liquid, rapid exchange of oxygen and carbon dioxide may be facilitated. Uses as heat exchangers in Microsystems by rapid evaporation of atomized droplets is another potential application area.

When the gas focusing flow cytometer cells of the subject invention have hydrophobic passages, liquid flow is focused and coherent. However, it has been discovered that if microfluidic cells of the same geometry but having hydrophilic passages are employed, the result is rapid and efficient atomization of the liquid stream rather than focusing.

The light source and light impingement system may comprise a conventional laser, numerous types of which are commercially available. With such lasers, optical systems are generally necessary to properly direct the laser beam through the interrogation zone. In this type of light supply, conventional auxiliary components can be used. "Auxiliary" components include conventional optics including but not limited to lenses, lens systems, filters, gratings, beam splitters, etc. These auxiliary components comprise the light impingement system when standard light sources are used. The light source may emit a range of light, may be monochromatic, or may be multichromatic.

Similarly, conventional light collection systems and light detection systems can be used. These include, generally, a photomultiplier tube or equivalent device as part of the detector system, generally also associated with auxiliary components such as lenses or lens systems, beam splitters, filters, gratings, etc., which also comprise the light collection system. The output of the photomultiplier and of photodiodes, when used, are generally connected to standard data acquisition devices and processed using analog or digital circuitry to maximize the signal to noise ratio. These techniques are easily implemented by those skilled in the art based on the concepts presented herein. For example, a noise baseline may be established, and only peaks projecting above this baseline may be reported.

When lenses or lens systems are employed, these may be external to the flow cell, or may be cast or inserted into the flow cell to minimize the number of external auxiliary components. The impingement and collection pathways terminate internally such that light impinges upon the collection zone, and is detectable following passage through the collection zone by the detector. The pathways for conventional impingement and collection pathways generally terminate "proximate" to the interrogation zone. For transparent devices, for example of acrylic resin or polyorganosiloxane, the path termini may be at an outside wall of the device, or may be located in close proximity to the interrogation zone, with an optically transparent passage, for example a hole, transparent rod or window, etc., whose innermost closed end is close to the interrogation zone. The actual construction of the impingement and collection zones is not critical so long as their function is achieved. It should be noted that the material of construction, if optically transparent at the desired wavelengths, may be structured in the form of a lens element or grating.

The present invention is further directed to novel light sources, light impingement systems, light collection systems, and light detector systems, which can be used to the exclusion of conventional system components, or in conjunction therewith.

To reduce size and cost, it is particularly preferred that the conventional light source be supplanted by one or more solid state "laser" diodes, which are preferably located within or on the flow cell or a housing thereof. Use of such devices is made practical by a novel light impingement system which employs optical waveguides, preferably fiber optics. In this preferred embodiment, the light from a laser diode light source is transmitted to the proximity of the interrogation zone by fiber optics. The optical fiber(s) terminate as close as possible to the interrogation zone to minimize scattering effects, for example terminating from 10 to 100 μm, preferably 30–80 μm from the interrogation zone. Due to the nature of the signal carrying capabilities of the optical fibers, lens systems which are commonly used in conventional systems may be eliminated, thus providing significant savings in size and cost, to the degree that in a preferred embodiment, the laser diode light source(s) may be incorporated within the body of the flow cell itself or intimately associated therewith, for example in a compact case, such that the entire device is portable, handholdable, and/or disposable. In addition to focusing fluid and sample fluid connections, only standard electrical connections need be provided, which can constitute metal contacts, jacks, etc.

The light impingement system can also be used with a remotely located light source, either of the conventional laser type or a laser diode type. In such cases, the optical fibers embedded within the body of the flow cell are preferably terminated at the exterior of the cell body, for example by conventional fiber optics coupling devices.

In like manner, the light collection system may comprise fiber optics as well, and preferably does so for purposes of miniaturization and disposability. As in the case of the light impingement systems, the optical fibers may be connected to an external detector, for example a photomultiplier tube and auxiliary components desired to maximize the signal to noise ratio. However, the fiber optics may also be connected to a detector system "on board," which allows for an integrated transportable and even handheld device. The configuration is also self-locating and fixtured, which minimizes the potential for interfering vibrations during measurements with a miniaturized device.

The novel detector system of the present invention is used in conjunction with an optical waveguide or fiber optic collection system, and comprises a semiconductor detector, preferably a PIN diode. Such diodes are commercially available, are capable of being biased by relatively low voltages, and are of relatively small size and cost. The PIN diode preferably includes one or more filters grown directly on the PIN structure or attached thereto. Such a filter is useful for filtering out extraneous light. For example, the filter may allow light of a fluorescence wavelength to pass while filtering out the wavelength used to excite the fluorescent species, for example a dye marker. Alternatively, an optional filter may be contained in the collection pathway as a component of a collimating lens system.

Figure 14A:
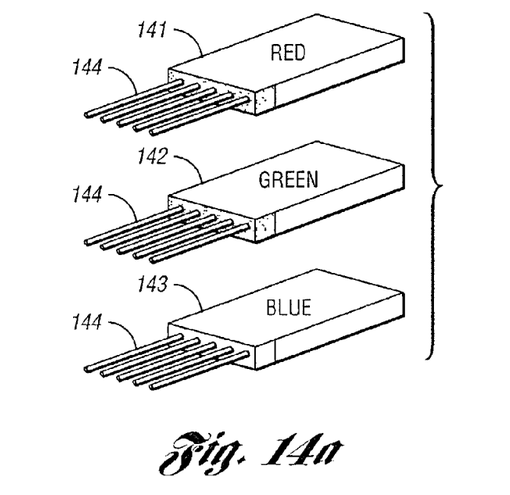
FIGS. 14a–14c illustrate a laser diode multichromatic light source canister for use in one embodiment of the subject invention.
Figure 14B:
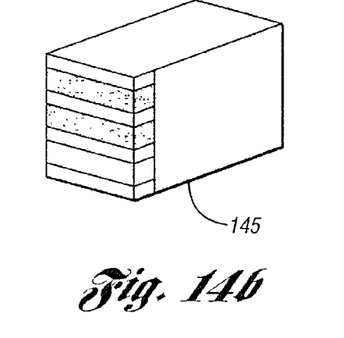
Figure 14C:
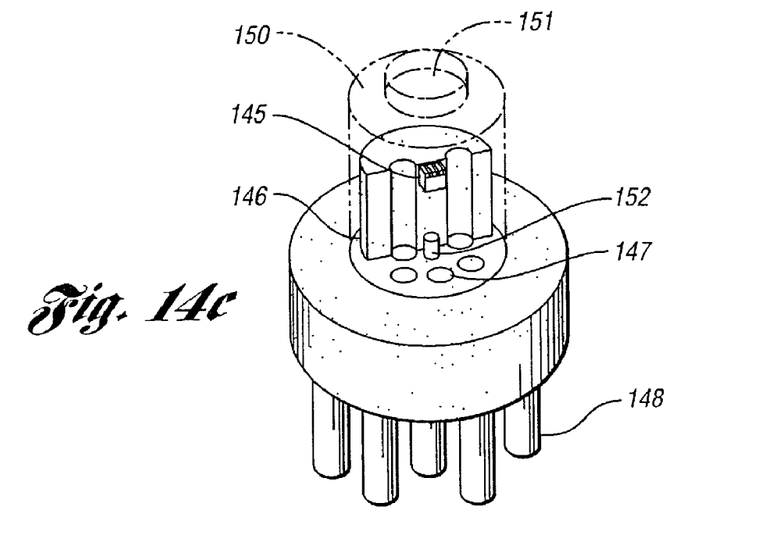

A multichromatic laser may suitably be configured into a canister assembly, and may take the form shown in FIGS. 14a–c. In these Figures, 141, 142, and 143 constitute different monochromatic solid state lasers, i.e. red, green, and blue, with attached electrical leads 144. The three laser diode chips are bonded into an integrated assembly 145 which may be mounted (FIG. 14c) on a heat sink 146, the leads connected to appropriate bond pads 147, in electrical communication with connector pins 148. The leads are not shown as connected to the bond pads in FIG. 14c for purposes of clarity. The laser assembly and heat sink are mounted on canister base 149 and encapsulated with a standard encapsulant or cover 150, the cover or encapsulant having a collimating lens 151, and preferably a coupling (not shown for clarity) for a fiber optic cable or optical waveguide to direct light from the laser diode canister to the light impingement path. An optional monitoring photodiode 152 may also be employed.

Figure 15A:
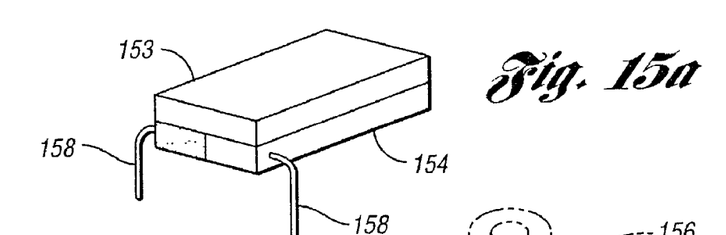
FIGS. 15a–15b illustrate a filtered photodiode detector canister for use in one embodiment of the subject invention.
Figure 15B:
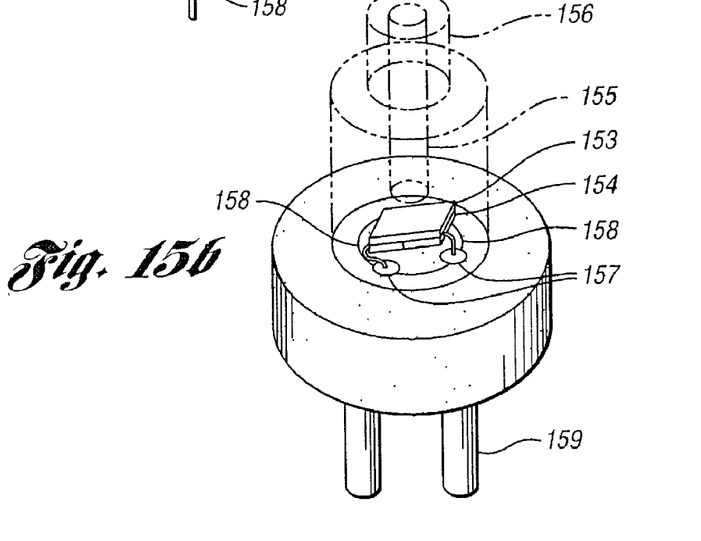

In a similar manner, a detector canister is shown in FIGS. 15a and 15b. This cannister contains a PIN photodiode 154, on top of which is mounted or integrally fabricated an optional filter or set of filters 153. Similarly to the photodiode canister, light is channeled to the photodiode by light pipe or optical wave guide 155, and secured thereto by connector 156. The photodiode leads 158 are secured to bonding pads 157 which in turn communicate electrically with pin connectors 159. Both the laser diode assembly and photodiode assembly can be mounted in the same canister, fabricated together on a single substrate, or integrated into the body or housing of the flow cytometer.

Preferably, the flow cytometers of the present invention comprise a flow cytometer having an interrogation zone, monitoring of which is made possible by a light impingement system comprising one or more optical pathways which channel light to and from the interrogation zone. The optical pathways may constitute a hollow pathway through the device, terminating at or proximate to the interrogation zone, the pathways optionally coated with a coating which facilitates light transmission through the pathway and optionally blocks potentially interfering light. Optical pathways such as optical waveguides may also be used, including fiber optic waveguides. Thus, while prior and subsequent description is in part specific to optical fibers, it should be understood that optical pathways in general, and optical waveguides may also be used. In optical fiber embodiments, for example, the light impingement system may comprise optical fibers terminating internally proximate the interrogation zone, and a light collection system may also comprise optical fibers terminating internally proximate the interrogation zone. Either a standard laser or preferably a laser diode or suitably filtered LED light source is employed, and preferably a photodiode is used as the detector. In such systems, light filters, gratings, lens systems, etc. may be used to increase performance.

When a photodiode is used as the detector, it has been found advantageous to provide "lock-in" amplification to maximize sensitivity and signal to noise ratio. Lock-in amplification has not heretofore been applied in conjunction with the use of silicon-based photodiodes in flow cytometry. A schematic for such an amplification system is provided in FIG. 9, but other systems are useful as well. It has been found that such systems, when employing fiber optic impingement and collection, can generate a signal to noise ratio which exceeds that of a typical photomultiplier detection system without lock-in amplification. The amplification system can easily be implemented on a single chip or on a multi-chip module by conventional fabrication and assembly techniques. This system can also be encased within the cell body or in a case surrounding the cell, again facilitating easily transportable and even handheld devices. The circuit components are inexpensive and readily available or fabricatable.

Figure 10:
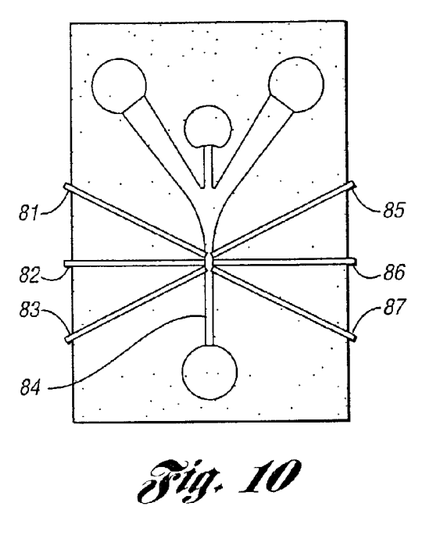
FIG. 10 illustrates an embodiment employing a plurality of fiber optic light impingement and/or collection paths of a flow cytometer cell or apparatus of the present invention.
Figure 11:
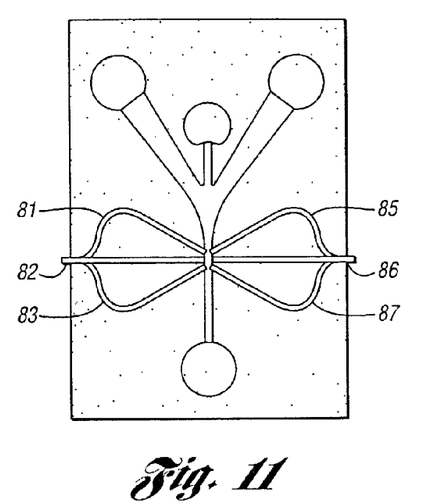
FIG. 11 illustrates one embodiment of a multiple path fiber optic impingement/collection path arrangement with single inputs and outputs.

The use of fiber optics as impingement and collection systems allows the use of multiple light paths in a single device, which has not been possible heretofore. For example, as shown in FIG. 10, multiple impingement/collection optical fibers may be imbedded in the flow cell. In FIG. 10, for example, "impingement" optical fibers 81, 82, and 83 terminate internally proximate the interrogation zone 84, while "collection" optical fibers 85, 86, and 87 also terminate proximate the interrogation zone. It has been discovered that for a given particulate, the oppositely opposed optical fibers 82, 86 do not necessarily provide the highest signal to noise ratio. Thus alternative light paths dictated by fiber pairs 81, 87; 83, 85; or 81, 83 may be used instead, or all may be used collectively with advanced signal processing techniques to deliver a high quality output. In addition, while each optical fiber (or fiber bundle) may carry but a single wavelength or multiple wavelengths (i.e. red/blue), the multiple paths allowable by this aspect of the invention allow different optical fiber pairs to carry distinct wavelengths. For example, optical fiber 81 may impinge red light upon the interrogation zone, collected by optical fiber 86 and/or 87, while optical fiber 83 may impinge blue light, collected by optical fiber 85. The optical fibers common to impingement and those common to collection may be bundled together at their termini remote from the interrogation zone to allow for a single source and single detector, as shown with reference to FIG. 11. The single source may be monochromatic or multichromatic. Designation of pathways in FIGS. 10 and 11 as "impingement" or "collection" is for purposes of illustration only.

While embodiments of light impingement and collection pathways have been illustrated herein in a relatively planar array, i.e. coinciding with the plane of the overall device and including the interrogation zone within this plane, it should be understood that light impingement and collection paths may also be located in a plane orthogonal to the axis of the interrogation zone, or in a plane skewed from the orthogonal plane and through which the axis of the interrogation zone passes. In other words, the arrangement of the light impingement and collection pathways is entirely flexible.

The light sources, when used in conjunction with a semiconductor detector, are preferably modulated, for example at frequencies of 10 Khz to 10 MHZ, more preferably 50 Khz to 500 Khz. A modulation frequency of 100 Khz has been found quite suitable. When n-multiple multichromatic light is involved, it is preferable that the signals be out of phase by 180° when two wavelengths are used, and 360°/n when n>2 frequencies are used. The different colors are preferably supplied as pulses separated by time with respect to color. For example, when red (R), green (G) and blue (B) emission is used, the light train may consist of repetitive RGB,RGB,RGB sequences, with the amplifier providing separate outputs for each color. When multichromatic light is employed with a plurality of suitably filtered photodiodes, each sensitive to a particular wavelength as a result, out of phase emission can be dispensed with.

While the novel light source, impingement system, collection system, and detector as described herein are useful with the gas-focusing flow cytometer as described previously, it also has utility in conventional liquid-focusing flow cytometers as well. Thus, the subject invention further pertains to a flow cytometer where a choice between gas-focusing and liquid-focusing cells may be made, and the flow cytometer apparatus reconfigured easily from one focusing mode to the other. For example, a given flow cytometer may be easily reconfigured from a gas-focusing cytometer to a liquid-focusing flow cytometer and vice versa by means of simply substituting a hydrophobic flow cell (gas focusing) with a hydrophilic flow cell (liquid focusing). This reconfiguration may be arranged in a simple manner so as to be reconfigurable in the field as well as in a laboratory setting.

Detection systems employing semiconductor diodes, unlike photomultiplier tubes, have no internal amplification, and the photocurrents generated may be in the range of 10 nA. Since noise interfering with a fluorescence signal associated with particle presence is directly proportional to the square root of the system bandwidth, minimization of this bandwidth is important in obtaining a high signal to noise ratio.

The particles traversing the interrogation zone have a velocity which is largely dependent upon the fluid flow rate through the cell. Typically, a maximum residence time at an interrogation point within the interrogation zone is about 10 μs, thus reflecting a minimum detection frequency of 100 KHz.

Figure 9:
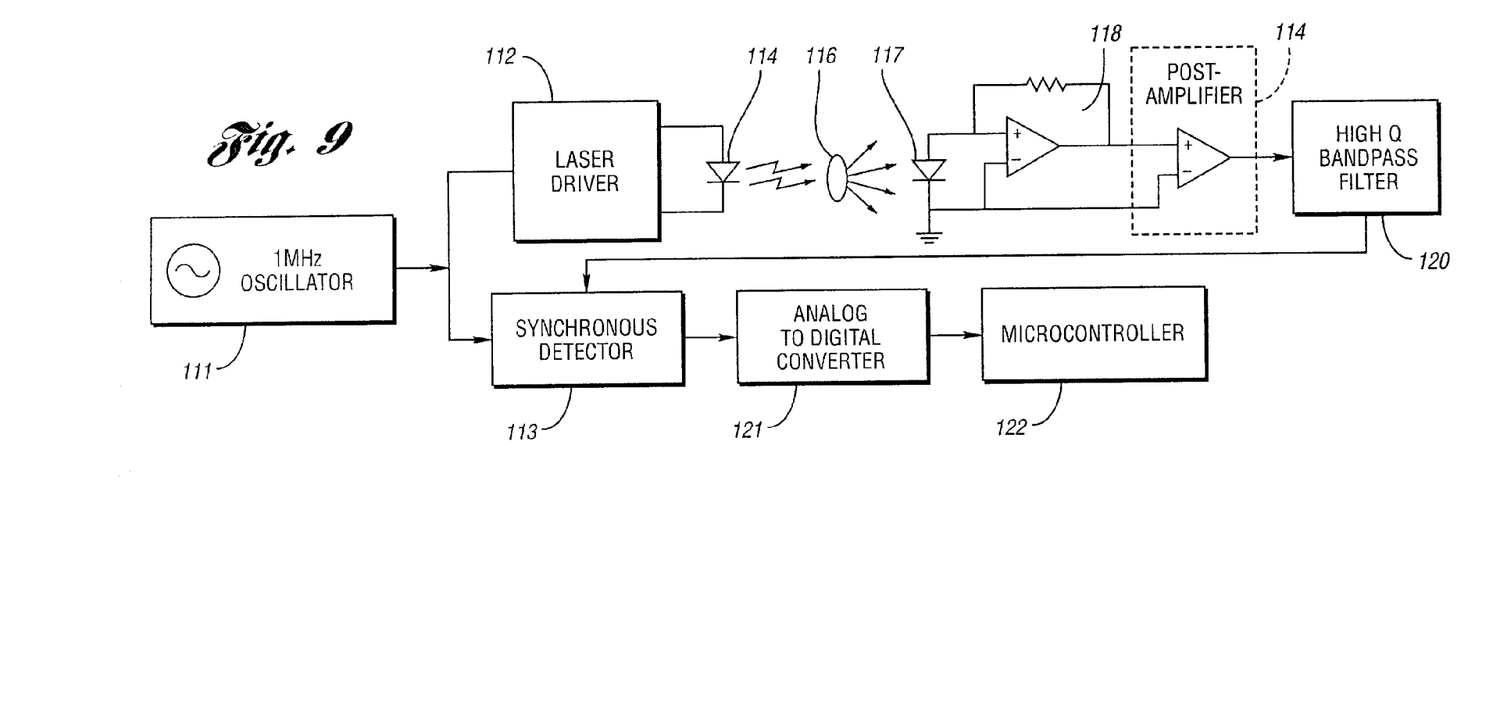
FIG. 9 illustrates one embodiment of an amplification system useful with the flow cytometer cells and apparatus of the present invention.

FIG. 9 illustrates a schematic of a synchronous ("lock in") detection system which can be assembled with conventional components. A 1 MHZ oscillator 111 is chosen to provide signal to both the laser driver 112 and synchronous detector 113. The laser driver provides a suitable driving signal for laser diode or LED 114, causing it to emit pulses of light at the 1 MHZ signal rate. The laser light, upon contacting a particle 116 in the interrogation zone causes a fluorescent output which is detected by PIN photodiode 117. The resulting electrical signal is amplified by a low noise differential amplifier 118, and optionally further amplified by additional amplifier(s) 119. The amplified signal is routed to a high Q (e.g. Q≅100) bandpass filter 120, which may, for example, limit the output signal to the range of 995 KHz to 1.005 MHZ, only a 10 KHz bandwidth. This output signal from the bandpass filter is routed to the synchronous detector 113, the output of which may be digitized by analog to digital (A/D) converter 121, and the data subsequently processed and/or collected by microcontroller or microcomputer 122.

Figure 13A:
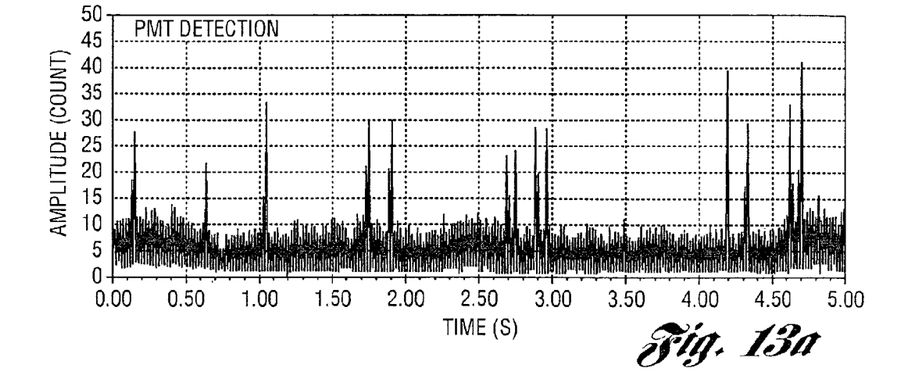
FIGS. 13a and 13b illustrate the signal of one embodiment of a flow cytometer employing a semiconductor detector and synchronous amplification as compared with a photomultiplier tube detector.
Figure 13B:
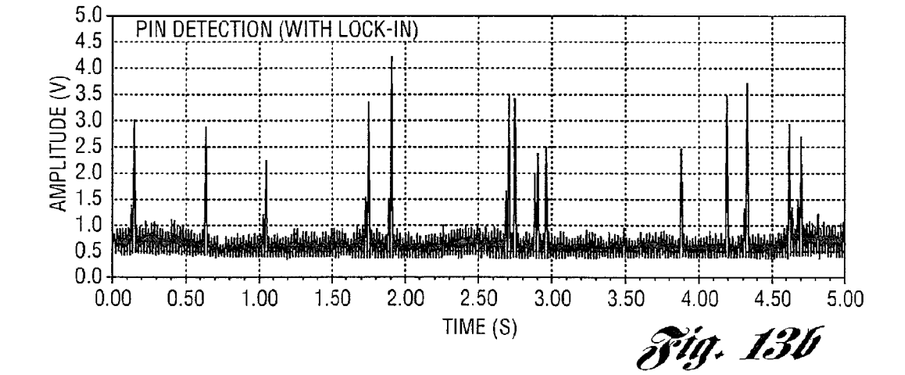

The output of a test device employing but single impingement and collection channels and a PIN detector with a 100 MHZ frequency rate was compared with that of a similar device employing a photomultiplier tube without lock-in amplification. The results are presented in FIGS. 13a and 13b, where the signal to noise ratio of the PIN detector (13b) is compared to that of the photomultiplier tube detector (13a). As can be seen, the signal to noise ratio of the subject invention device, even at this early stage in its development, is very good. All particles detected by the photomultiplier tube were detected with the PIN diodes.

Figure 12:
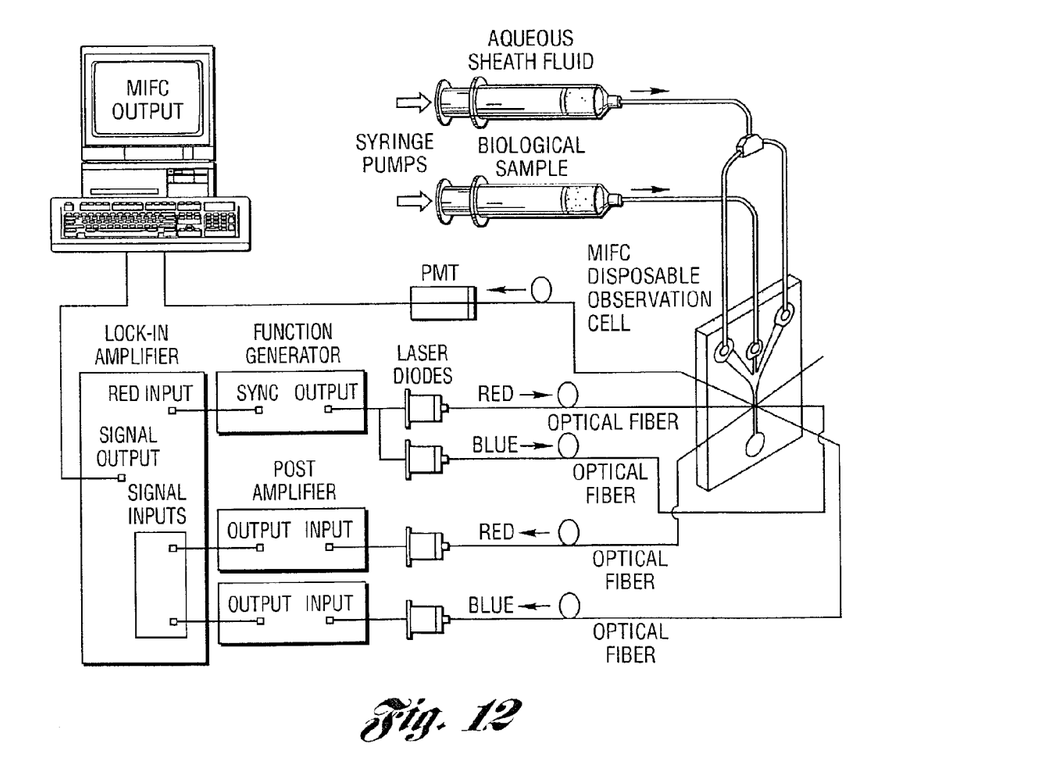
FIG. 12 illustrates a schematic of a synchronous amplification system useful with a semiconductor photodetector.

It is expected that additional signal processing will further improve the signal to noise ratio, as will the possibility of employing multiple wavelength light sources and multiple or selected collector channels. For example, a liquid-focusing flow cytometer employing fiber optic impingement and collection and further employing both red and blue light sources and a redundant photomultiplier tube (PMT) for comparison purposes is illustrated in FIG. 12, where "MIFC" stands for microintegrated flow cytometer.

Regardless of the nature of the light collection pathways, for example whether of simple open paths, wave guides in general, or more specifically fiber optics, and regardless of the overall nature of the flow cytometer, i.e. whether conventional, air focusing, liquid focusing, and regardless of the nature of the detection system, the lock-in amplification system of the present invention may be used to maximize signal to noise ratio at one or more detection wavelengths. The lock-in amplification may be effected by a phase lock loop approach or any other approach wherein amplification is performed synchronously with light impingement. The specific embodiments described herein should not be construed as limiting the scope of the invention in any way.

The gas-focusing flow cells of the subject invention have additional uses beyond flow cytometry. For example, the focusing liquid may contain a chromophoric indicator for the presence of a particular gas in the flow focusing stream, for example carbon monoxide. If the focusing gas contains carbon monoxide, the liquid stream will change color, a change detectable by the optical systems described herein or other detection systems. Further, as with atomized samples, due to its small diameter, the liquid stream has a relatively high surface to volume ratio which facilitates heterogenous reactions such as hydrogenation, etc. Further applications include cell sorting, use as an artificial lung, and massively parallel cell analysis. These uses are illustrative but not limiting, and the designation of a subject invention microfluidics device as a flow cytometer cell should not be construed as not comprehending its use in other areas of microfluidics as described herein.

While embodiments of the invention have been illustrated and described, it is not intended that these embodiments illustrate and describe all possible forms of the invention. Rather, the words used in the specification are words of description rather than limitation, and it is understood that various changes may be made without departing from the spirit and scope of the invention.

What is claimed is:

1. A flow cytometer cell, comprising
 a) fluid sample inlet comprising a fluid sample channel;
 b) at least one focusing fluid inlet comprising a fluid focusing channel;
 c) a convergent focusing zone, said fluid sample channel and said fluid focusing channel communicating with an upstream end of said convergent focusing zone, said convergent focusing zone narrowing to form an inlet to an interrogation zone;
 d) an interrogation zone, said interrogation zone comprising a channel through which sample fluid enveloped by focusing fluid flows, said interrogation zone terminating in an outlet, further comprising at least three optical waveguide light impingement and/or collection path(s), internal ends of said optical waveguide light path(s) terminating at or proximate to said interrogation zone, an opposing end of said optical waveguide light path(s) in communication with or adapted to be placed in communication with a light source or a photodetector, said at least three fiber optic waveguides comprising at least a first fiber optic wave guide illuminating said interrogation channel, and at least two fiber optic waveguides conveying light from said interrogation channel to at least one detector, said three fiber optic waveguides all located in a plane which includes the interrogation channel.

2. A flow cytometer cell, comprising
 a) a fluid sample inlet comprising a fluid sample channel;
 b) at least one focusing fluid inlet comprising a fluid focusing channel;
 c) a convergent focusing zone, said fluid sample channel and said fluid focusing channel communicating with an upstream end of said convergent focusing zone, said convergent focusing zone narrowing to form an inlet to an interrogation zone;
 d) an interrogation zone, said interrogation zone comprising a channel through which sample fluid enveloped by focusing fluid flows, said interrogation zone terminating in an outlet, further comprising at least three optical waveguide light impingement and/or collection path(s), internal ends of said optical waveguide light path(s) terminating at or proximate to said interrogation zone, an opposing end of said optical waveguide light path(s) in communication with or adapted to be placed in communication with a light source or a photodetector, said at least three fiber optic waveguides comprising at least two fiber optic wave guides illuminating said interrogation channel, and at least one fiber optic waveguide conveying light from said interrogation channel to at least one detector, said three fiber optic waveguides all located in a plane which includes the interrogation channel.

* * * * *